United States Patent [19]
Leung et al.

[11] Patent Number: 6,010,714
[45] Date of Patent: Jan. 4, 2000

[54] NON-THERMOGENIC HEAT DISSIPATING BIOMEDICAL ADHESIVE COMPOSITIONS

[75] Inventors: Jeffrey C. Leung; Jeffrey G. Clark, both of Raleigh, N.C.

[73] Assignee: Closure Medical Corporation, Raleigh, N.C.

[21] Appl. No.: 08/755,007

[22] Filed: Nov. 22, 1996

[51] Int. Cl.$^7$ .................................................. A61F 13/02
[52] U.S. Cl. ........................ 424/448; 424/443; 424/449; 424/484; 424/485; 424/486; 424/78.35; 604/892.1
[58] Field of Search .................................... 424/443, 448, 424/449, 484, 485, 486, 78.35; 604/892.1; 514/562, 563, 442, 617, 620

[56] References Cited

U.S. PATENT DOCUMENTS

| | | | |
|---|---|---|---|
| 2,721,858 | 10/1955 | Joyner et al. | 260/67 |
| 2,768,109 | 10/1956 | Coover, Jr. et al. | 154/133 |
| 3,254,111 | 5/1966 | Hawkins et al. | 260/465.4 |
| 3,527,841 | 9/1970 | Wicker, Jr. et al. | 260/823 |
| 3,554,990 | 1/1971 | Quinn et al. | 260/88.7 |
| 3,559,652 | 2/1971 | Banitt et al. | 128/334 |
| 3,722,599 | 3/1973 | Robertson et al. | 128/334 R |
| 3,759,264 | 9/1973 | Coover, Jr. et al. | 128/334 R |
| 3,940,362 | 2/1976 | Overhults | 260/42.16 |
| 3,995,641 | 12/1976 | Kronenthal et al. | 128/335 |
| 4,042,442 | 8/1977 | Dombroski et al. | 156/310 |
| 4,131,597 | 12/1978 | Bluethgen et al. | 260/42.18 |
| 4,187,559 | 2/1980 | Grell et al. | 3/1.91 |
| 4,364,876 | 12/1982 | Kimura et al. | 260/465.4 |
| 4,578,061 | 3/1986 | Lemelson | 604/164 |
| 4,793,330 | 12/1988 | Honeycutt et al. | 128/90 |
| 4,832,688 | 5/1989 | Sagae et al. | 604/53 |
| 4,852,568 | 8/1989 | Kensey | 128/325 |
| 4,890,612 | 1/1990 | Kensey | 606/213 |
| 4,900,303 | 2/1990 | Lemelson | 604/54 |
| 4,900,546 | 2/1990 | Posey-Dowty et al. | 424/81 |
| 5,021,059 | 6/1991 | Kensey et al. | 606/213 |
| 5,053,046 | 10/1991 | Janese | 606/215 |
| 5,061,274 | 10/1991 | Kensey | 606/213 |
| 5,108,421 | 4/1992 | Fowler | 606/213 |
| 5,129,882 | 7/1992 | Weldon et al. | 604/96 |
| 5,192,300 | 3/1993 | Fowler | 606/213 |
| 5,221,259 | 6/1993 | Weldon et al. | 604/96 |
| 5,222,974 | 6/1993 | Kensey et al. | 606/213 |
| 5,258,420 | 11/1993 | Posey-Dowty et al. | 523/116 |
| 5,275,616 | 1/1994 | Fowler | 606/213 |
| 5,282,827 | 2/1994 | Kensey et al. | 606/215 |
| 5,292,332 | 3/1994 | Lee | 606/213 |
| 5,319,011 | 6/1994 | Schoon | 524/261 |
| 5,324,306 | 6/1994 | Makower et al. | 606/213 |
| 5,328,687 | 7/1994 | Leung et al. | 424/78.35 |
| 5,330,446 | 7/1994 | Weldon et al. | 604/271 |
| 5,370,660 | 12/1994 | Weinstein et al. | 606/215 |
| 5,372,585 | 12/1994 | Tiefenbrun et al. | 604/59 |
| 5,401,508 | 3/1995 | Manesis | 424/427 |
| 5,582,834 | 12/1996 | Leung et al. | 424/426 |
| 5,817,708 | 10/1998 | Congelio et al. | 524/104 |

OTHER PUBLICATIONS

Agah, R. et al., "Rate Process Model for Arterial Tissue Thermal Damage: Implications on Vessel Photocoagulation", *Lasers in Surgery and Medicine,* vol. 15, pp. 176–184 (1994).

*Primary Examiner*—S. Mark Clardy
*Assistant Examiner*—Kathryne E. Shelborne
*Attorney, Agent, or Firm*—Oliff & Berridge, PLC

[57] ABSTRACT

A biocompatible monomer composition includes at least one monomer, which forms a medically acceptable polymer, and an effective amount of at least one heat dissipating agent sufficient to reduce exothermic polymerization temperature increase of the composition. The heat dissipating agent enhances patient comfort and prevents necrosis of living tissue normally encountered with such medical adhesives.

32 Claims, No Drawings

NON-THERMOGENIC HEAT DISSIPATING BIOMEDICAL ADHESIVE COMPOSITIONS

BACKGROUND OF THE INVENTION

1. Field of the Invention

This invention relates to monomer compositions useful in the formulation of biomedical adhesives and sealants, and methods of applying them to living tissue. More particularly, this invention relates to wound closure monomer compositions and their use for medical, surgical and other internal and external applications.

2. Background

Numerous methods and materials have been developed for biomedical sealants and adhesives including, for example, application to skin, hemostatic sealing of punctures and incisions in various living tissue, internal organs and blood vessels. For example, some of these methods utilize clotting agents, as set forth in U.S. Pat. Nos. 5,129,882 to Weldon et al., 5,221,259 to Weldon et al., and 5,330,446 to Weldon et al.; biocompatible adhesives cured or sealed by electromagnetic radiation, as set forth in U.S. Pat. No. 5,372,585 to Tiefenbrun; porous biodegradable patches or gauze, as set forth in U.S. Pat. Nos. 4,900,303 and 4,578,061 both to Lemelson; and plugs in the puncture sites of the vessel or organ, as set forth in U.S. Pat. Nos. 5,370,660 to Weinstein et al., 5,324,306 to Makower et al., 5,292,332 to Lee, 4,832,688 to Sagae et al., 5,053,046 to Janese, 5,108,421, 5,275,616, and 5,192,300 all to Fowler, and 4,852,568, 4,890,612, 5,061,274, 5,222,974, 5,282,827 and 5,021,059 all to Kensey et al. The subject matter of these patents is incorporated herein by reference.

Adhesives have been proposed as wound closure devices. One group of such adhesives is the monomeric forms of alpha-cyanoacrylates. Reference is made, for example, to U.S. Pat. Nos. 5,328,687 to Leung et al; 3,527,841 to Wicker et al.; 3,722,599 to Robertson et al.; 3,995,641 to Kronenthal et al.; and 3,940,362 to Overhults, which disclose alpha-cyanoacrylates that are useful as surgical adhesives. All of the foregoing references are hereby incorporated by reference herein.

Typically, the cyanoacrylate surgical adhesive is applied to one or both surfaces of wounds or incisions, including the internal portions of the wound, with any excess adhesive being quickly removed from the bonding surfaces. Subsequently, the edges of the wound are held together until they adhere. See U.S. Pat. No. 3,759,264 to Coover, Jr. et al.

A topical tissue adhesive commercially available is Histoacryl® available from B. Braun Melsungen AG of Germany. The manufacturer recommends use of this adhesive only for closure of minor skin wounds and not for internal use. Moreover the manufacturer recommends that the adhesive be used sparingly or in thin films because thick films do not increase the film strength and can lead to necrosis of surrounding tissue due to thermogenic reaction. Moreover, films formed from this adhesive are brittle, permitting severe dehiscence of wounds.

Thermogenic reactions of the above-mentioned tissue adhesives cause thermal damage (i.e., necrosis) of the tissue surrounding the adhesive upon which it is applied. Thermal damage to arterial tissue is described in an article entitled "Rate Process Model For Arterial Tissue Thermal Damage," *Lasers In Surrerv And Medicine*, vol. 15, pages 176–184, 1994. The primary effect heat has on arterial tissue is the denaturation of proteins. Collagen, one of the most abundant proteins in living tissue, has a relatively low denaturation threshold at 62–67° C. The heating period for inducing thermal lesion in human aorta may range from 5 seconds at 73° C. to 14.5 minutes at 66° C.

Accordingly, there is a need for a surgical adhesive that does not cause thermal damage or necrosis of living tissue after application of the adhesive to the tissue.

Various methods and materials have been utilized in different applications that reduce heat of exothermic reactions, albeit not as biomedical adhesives or sealants. For example, U.S. Pat. No. 4,131,597 to Blüethgen et al. discloses a bioreactive composite material for prosthetic purposes. Heat of polymerization may be removed by rinsing, washing or irrigating with a biocompatible, nonaggressive, sterile cooling liquid.

U.S. Pat. No. 5,319,011 to Schoon discloses cyanoacrylate polymers and the effect of heat formed during the exothermic polymerization of the monomer. When used as a surface coating for nails, the exothermic reaction may cause blistering and burning of the nails and skin underlying the nails. Reduction of the heat generated may be accomplished using an organotin catalyst, which alters the exothermic nature of polymerization. U.S. Pat. No. 5,401,508 to Manesis discloses a hydrogel composition comprising water and a copolymer (abstract). The polymerization may be carried out in the presence of a small amount of a solvent to improve conversion and to flatten the exotherm peak. The polymerization is conducted in a mold and not in situ. Reaction exotherms are controlled to eliminate stress cracking and to obtain optimum conversion of monomers. U.S. Pat. Nos. 4,900,546 and 5,258,420, both issued to Posey-Dowty et al., disclose a bone cement for sustained release of therapeutic substances. The cement composition comprises a liquid monomer and therapeutic substances. An emulsifier may also be added to the cement composition, which also serves to dissipate the heat formed during exothermic polymerization of the monomer. The emulsifier is mixed in the monomer in an amount of about 0.1 to about 10.0 wt. % The cement is applied to bone and subsequently polymerized. U.S. Pat. No. 4,042,442 to Dombroski et al. discloses alphacyanoacrylate adhesive compositions and initiators for promoting the polymerization of adhesive compositions. The polymerization of the adhesive compositions may be accelerated by either treating the surface to be bonded with a basic material or by adding a small amount of a basic catalyst to the adhesive just prior to use.

U.S. Pat. No. 3,995,641 to Kronenthal et al. discloses carbalkoxyalkyl 2-cyanoacrylates as surgical adhesives (abstract). The heat of polymerization and the time required to reach maximum exotherm is also disclosed. Use of a carbalkoxyalkyl component modifies the chemical reaction mechanism. U.S. Pat. No. 4,793,330 to Honeycutt et al. discloses an orthopedic cast system wherein a fabric treated with wax is used to absorb the heat of exothermic reaction. The waxes may be used in combination with solvents or emulsifiers. An α-cyanoacrylate is utilized as a hardening agent and not as an adhesive. Additionally, the cyanoacrylate does not come into direct contact with the skin because a barrier fabric is placed on the skin prior to application of the cyanoacrylate. U.S. Pat. No. 4,187,559 to Grell et al. discloses a body joint endoprosthesis. The patent also discloses the effect of the heat of polymerization of a monomer on a tissue. The monomer is used to cement implants to the bone. To eliminate the negative effects of excessive heat, the cement is eliminated from the implant procedure altogether.

Other methods utilize various materials to catalyze surfaces to initiate polymerization of monomeric compositions.

U.S. Pat. No. 3,759,264 to Coover, Jr. et al. discloses a surgical α-cyanoacrylic acid adhesive for joining tissue surfaces together. Catalysts or accelerators may be used to rapidly form a bond. The catalysts are normally applied to the surfaces of the tissues to be bonded with subsequent application of the adhesive. Suitable polymerization catalysts or accelerators include solutions of aliphatic alcohol, such as methanol, isobutanol, capryl, etc. U.S. Pat. No. 2,768,109 to Coover, Jr. discloses a method of bonding a material exhibiting an acidic surface character, which comprises moistening the surface to be bonded with an alkyl monohydric alcohol bonding promoter and thereafter applying to the surface a film of an adhesive composition comprising alpha cyanoacrylate monomer. A high volatile bonding promoter is used to enable evaporation of the promoter and thereby eliminate excess promoter. The cyanoacrylates are used in bonding a variety of materials.

SUMMARY OF THE INVENTION

The present invention is based on the discovery that combining the monomers described hereinafter with a heat dissipating agent provides a surgical adhesive or sealant that, after application to living tissue, polymerizes to form a strong and flexible bond in or on the living tissue without causing necrosis due to thermogenic effects of the living tissue. Furthermore, the present invention provides a process for application of this surgical adhesive or sealant composition to living tissue to provide a polymerized composition thereon while minimizing or reducing the temperature increase of the composition due to the polymerization reaction.

The surgical adhesives or sealants may be applied in vivo to living tissue and are biocompatible with the tissue. The adhesives or sealants may be bioabsorbable and may be applied internally or externally in or on the living tissue.

DETAILED DESCRIPTION OF THE PREFERRED EMBODIMENTS

One embodiment of the present invention includes a biomedical adhesive or sealant composition, comprising:
A) at least one monomer, which forms a medically acceptable adhesive or sealant polymer; and
B) an effective amount of at least one heat dissipating agent sufficient to reduce exothermic polymerization temperature increase of the composition. The term "medically acceptable" in this context includes all polymers that are suitable for use on or in living tissue.

In other embodiments, the present invention is directed to methods of using the above-described monomers, copolymers and polymers made therefrom for biomedical purposes.

The adhesive composition of the present invention may be applied internally or externally. The composition, when applied internally, may be bioabsorbable without causing histotoxicity of the living tissue.

Multiple applications or layers of the surgical adhesive may be applied in succession. For example, after application of a first layer of adhesive, the layer is allowed to at least partially polymerize and a subsequent layer of adhesive may be applied over the first layer. Such a process could be conducted numerous times, depending on the size of the puncture or incision and the amount of adhesive applied in each application.

The surgical adhesive may be applied using a variety of dispensing devices. Depending on the particular requirements of the user, the adhesive compositions of this invention can be applied by known means such as with a glass stirring rod, sterile brush or medicine dropper. However, in many situations a pressurized aerosol dispensing package is preferred in which the adhesive composition is in solution with a compatible anhydrous propellant.

Suitable applicators for application of the adhesive of the present invention include those described in copending U.S. patent application Ser. No. 08/488,411, the subject matter of which is incorporated herein by reference. The surgical adhesive may also be applied using the devices set forth in U.S. Pat. Nos. 4,900,303 to Lemelson and 5,372,585 to Tiefenbrun while monitoring the application process through an optical viewing system. The adhesive of the present invention may also be applied by the devices set forth in U.S. Pat. No. 5,129,882 to Weldon et al. or with the devices set forth in U.S. patent application Ser. No. 08/609,921. The subject matter of these documents is incorporated herein by reference. A preferable applicator is a crushable swab applicator.

The adhesive compositions of this invention and polymers formed therefrom are useful as tissue adhesives, sealants for preventing bleeding or for covering open wounds, and in other biomedical applications. They find uses in, for example, apposing surgically incised or traumatically lacerated tissues; setting fractured bone structures; retarding blood flow from wounds; aiding repair and regrowth of living tissue; and as a drug delivery matrix.

The surgical adhesive according to the present invention may also be applied in conjunction with other sealing means. For example, the adhesive may be applied to puncture sites that have been closed using surgical suture or tape, such as in the sealing of a puncture or incision in internal organs, e.g., liver, gallbladder, intestines, stomach, kidney, heart, urinary bladder, ureter, lung, esophagus and the like. The adhesive will provide a complete seal, thereby reducing the risk of body fluid leakage from the organ or vessel, e.g., leakage from liver puncture sites. The surgical adhesive of the present invention may additionally be used in conjunction with other sealing means, such as plugs, and the like. Such techniques are set forth in U.S. Pat. Nos. 4,852,568 to Kensey, 4,890,612 to Kensey, 5,053,046 to Janese, 5,061,274 to Kensey, 5,108,421 to Fowler, 4,832,688 to Sagae et al., 5,192,300 to Fowler, 5,222,974 to Kensey et al., 5,275,616 to Fowler, 5,282,827 to Kensey et al., 5,292,332 to Lee, 5,324,306 to Makower et al., 5,370,660 to Weinstein et al., and 5,021,059 to Kensey et al. The subject matter of these patents is incorporated herein by reference.

The adhesive composition of the present invention may also be applied topically or externally. In one such embodiment, the edges of a wound or incision are held together and an excessive amount of the above-described surgical adhesive composition is applied to the already pinched or abutted opposing wound edges, preferably utilizing more than one application stroke. This process forms a bridge over the abutted opposing wound edges that is flexible and possesses high tensile strength. The excessive amount of adhesive placed on the abutted opposing wound edges forms a thick film thereon and unexpectedly increases film strength.

Specific methods that may use an adhesive composition of the present invention include methods for repairing damaged living tissue to prevent the escape of fluids therethrough by holding damaged tissue edges together in an abutting relationship, applying to the abutting tissue the adhesive composition of the present invention, and allowing the composition to polymerize; methods for stemming the flow of blood from vessels, which comprises holding damaged regions of the blood vessels together, applying the present adhesive composition to the damaged regions and allowing the composition to polymerize; and methods of bonding bone tissue to promote healing of weak or fractured bones, which comprises holding damaged bone tissue together, applying to the damaged tissue the present adhesive composition, and allowing the composition to polymerize.

Repairing injured tissues (for example, to control bleeding) comprises, in general, sponging to remove superficial body fluids, holding injured tissue surfaces together in an abutting relationship and subsequent application to the exposed abutted tissue of the present adhesive composition. The composition polymerizes to a thin film of polymer while in contact with the abutted tissue surface. Tissues that are not bleeding or otherwise covered by body fluids need not be sponged first. More than one coating or application of adhesive composition may be applied to the abutted tissue surface.

Adhesive compositions used in the methods of the present invention preferably polymerize and/or cross-link in vivo, preferably without the need for external sources of physical initiation such as irradiation. In embodiments, for example, the polymerization and/or cross-linking may be initiated by contact with body tissues and fluids or by contact with a chemical initiator and/or exposure to a physical initiator immediately before application of the adhesive.

In other embodiments, for example, the heat dissipating agent may be mixed with a polymerization initiator and/or other components, such as thickeners, plasticizers, colorants, fillers, etc., and stored separately from the monomeric component. Subsequently, this mixture may be mixed with the monomeric component before or during application to the substrate or tissue. Alternatively, the heat dissipating agent may be premixed with the monomeric component and/or other additives described herein, in a composition having a shelf life.

The monomers of the adhesive composition are readily polymerized to addition-type polymers and copolymers, which are generally optically clear (as films).

In most bonding applications using the compositions of this invention, polymerization of the monomers is catalyzed by small amounts of moisture on the surface of the adherents; thus desired bonding of tissues or hemostasis proceeds well in the presence of blood and other body fluids. The bonds formed are of adequate flexibility and strength to withstand normal movement of tissue. In addition, bond strength is maintained as natural wound healing proceeds.

Following application to living tissue, the monomeric component of the composition polymerizes to yield a polymer or copolymer. During the polymerization process, an exothermic reaction occurs that increases the temperature of the composition. Depending on the monomer utilized in the composition and the additives used, the temperature increase varies. Additionally, polymerization initiators or accelerators increase the rate of polymerization of the monomer and, thus, increase the heat released and temperature rise during polymerization.

The increase in temperature of the composition due to exothermic polymerization of the monomeric component may be as low as 5° C. and as high as 70° C., depending on the monomer and initiator utilized and the mass applied. A temperature increase of as little as 40° C. of the adhesive composition placed on the surface of living tissue will generally cause necrosis or thermal damage. Temperature increases of lesser amounts will generally cause discomfort and irritation of the tissue.

In order to minimize these problems, heat dissipating agents of the present invention are introduced into the composition. The heat dissipating agents include liquids or solids that may be soluble or insoluble in the monomer. The liquids may be volatile and may evaporate during polymerization, thereby releasing heat from the composition. The liquids may include ethers, ketones, chlorofluorocarbons, alkanes, alcohols, alkenes and mixtures thereof. Esters, ketones, chlorofluorocarbons, and alkanes are preferred, and chlorofluorocarbons and ethers are more preferred.

Solid heat dissipating agents may also be utilized. For example, solids that melt or sublime at the polymerization temperatures of the monomeric component may be used. For example, solids that melt or sublime at temperatures of from about 20 to about 160° C. may be used, preferably from about 30 to about 150° C., and more preferably from about 40 to about 140° C. Depending on the monomer utilized, the polymerization temperature will vary. Generally, the higher the polymerization temperature the higher the melting point, sublimation point and boiling point of the heat dissipating agent should be.

Additionally, solids that act as a heat sink or that readily adsorb heat may be utilized. Suitable heat-adsorbing substances include alkaline metal oxide such as aluminum oxide, barium oxide, titanium oxide, manganese oxide and calcium oxide; metals such as copper, lead, nickel, aluminum, and zinc; carbon black and carbides; organic compounds such as urea, paraffin wax and polyvinyl fluoride; and salts such as ammonium nitrate, potassium nitrate, sodium acetate trihydrate, sodium sulfate decahydrate (Glauber's salt), barium hydroxide octahydrate, calcium oxalate dihydrate, magnesium oxalate dihydrate, aluminum hydroxide, ammonium sulfate, zinc sulfate, and ammonium phosphate. Of these, aluminum oxide, aluminum, Glauber's salt, and paraffin wax are preferred, and Glauber's salt and paraffin wax are more preferred.

Suitable sublimable substances (with their sublimation point (° C.) at atmospheric pressure in parentheses) include 2-hydroxy-2-trimethylsilanyl-propionitrile 60); ammonium salt of 2,2,4,6-tetrakis(trifluoromethyl)-1,2-dihydro-1,3,5-triazine (120–130); 1-fluoropentacyclo[6.3.0.02,6.03,10.05,9]undecane (100–110); 6,7-diazabicyclo[3.2.1]oct-6-ene (40); 5,5,6,6-tetramethylbicyclo[2.2.1]heptan-2-ol (102–108); complex of dimethyl magnesium and trimethylaluminum (40); bis-[2,2,2-trifluoroethyl]ammonium nitrate (140); complex of ammonia and boric acid trimethyl ester (45); N-benzyl-2,2,3,3,4,4,4-heptafluoro-butyramide (80); 3-isopropyl-5, 8a-dimethyl-decahydronaphthalen-2-ol (80); 2-hydroxymethyl-1,7,7-trimethyl-bicyclo[2.2.1]heptan-2-ol (100–105); 3,5-dichloro-3-methyl-cyclopentane-1,2-dione (110–120); (5-methyl-2-oxo-bicyclo[3.3.1.]non-3-en-1-yl)-acetic acid (140); 4b,6a,11,12-tetrahydro-indeno[2,1-a]fluorene-5,5,6,6-tetracarbonitrile (150); tetraccsafluoro-tetradecahydro-anthracene (60) ; 4,5-dichlorobenzene-1,2-dicarbaldehyde (30–40); bicyclo[4.3.1]dec-3-en-8-one (150); 3-tert-butyl-1,2-bis-(3,5-dimethylphenyl)-3-hydroxyguanidine (145); 1-[2,6-dihydroxy-4-methoxy-3-methyl-phenyl]butan-1-one (100); 2,3,6,7-tetrachloronaphthalene (135); 2,3,6-trimethylnaphthalene (80); dodecafluoro-cyclohexane (51–53); 2,2,6,6-tetramethyl-4-hepten-3-one (55); heptafluorobutyramide (80); pentafluoropropionamide (60); 1,1,1-trichloro-2,2,2-trifluoro-ethane (46); [5-(9H-beta-carbolin-1-yl)-furan-2-yl]methanol (150); 5-nitro-benzo[1,2,3]thiadiazole (80–100); 4,5-dichloro-thiophene-2-carboxylic acid (120); 2,6-dimethyl-isonicotinonitrile (50); nonafluoro-2,6-bis-trifluoromethyl-piperidine (50–60); krypton tetrafluoride (70); (dimethylamino) difluoroborane (130–135); difluorourea (25–35); uranium hexafluoride (57); dinitrogen pentoxide (33–34); chromyl fluoride (30); and chromium hexacarbonyl (25). 2,2,6,6-tetramethyl-4-hepten-3-one is preferred.

Suitable solids that melt (with their melting points (° C.) at atmospheric pressure in parentheses) include 1-methylcyclohexanol (24–26); phenyl ether (26–30); nonadecane (32–34); 1-tetradecanol (38–40); 4-ethylphenol (42–45); benzophenone (46–48); maleic anhydride (54–56); octacosane (61–63); dimethyl isophthalate (68–71); butylated hydroxytoluene (69–70); glycolic acid (75–80); vanillin (81–83); magnesium nitrate hexahydrate (89); cyclohexanone oxime (89–90); glutaric acid (95–98); D-sorbitol (98–100); phenanthrene (99–101); methacrylamide (109–111); fluorene (114–116); ammonium acetate (110–112); 4-hydroxybenzaldehyde (117–119); trans-stilbene (122–124); neopentyl glycol (123–127); pyrogallol (133–134); and diglycolic acid (142–145). Maleic anhydride is preferred.

There may be more than one heat dissipating agent added to the composition and may include a combination of solids and liquids, or a combination of only liquids or only solids.

The heat dissipating agent is preferably inert and does not affect the polymerization rate of the monomer (i.e., it does not increase or decrease the polymerization rate). Additionally, the heat dissipating agent does not negatively impact the strength and flexibility of the resulting polymeric material. The amount of heat dissipating agent added to the composition may vary depending on the monomer used and the heat dissipating agent used. Generally the amount added is about 0.1 wt. % to about 70 wt. %, preferably from about 1 wt. % to about 45 wt. %, and more preferably from about 2 wt. % to about 25 wt. % by weight of monomer.

Monomers that may be used in this invention are polymerizable, e.g. anionically polymerizable or free radical polymerizable, to form polymers. Such monomers include those that form polymers, which may, but do not need to, biodegrade. Preferred monomers include 1,1-disubstituted ethylene and derivatives thereof. Reference is made, for example, to U.S. Pat. No. 5,328,687, which is hereby incorporated by reference herein. As defined herein, "histotoxicity" refers to adverse tissue response, such as inflammation due to the presence of toxic materials in the tissue.

Useful 1,1-disubstituted ethylene monomers include, but are not limited to, monomers of the formula:

$$CHR\!=\!CXY \quad (I)$$

wherein X and Y are each strong electron withdrawing groups, and R is H, —CH=CH$_2$ or, provided that X and Y are both cyano groups, a C$_1$–C$_4$ alkyl group.

Examples of monomers within the scope of formula (I) include alpha-cyanoacrylates, vinylidene cyanides, C$_1$–C$_4$ alkyl homologues of vinylidene cyanides, dialkyl methylene malonates, acylacrylonitriles, vinyl sulfonates and vinyl sulfonates of the formula CH$_2$=CX'Y' wherein X' is —SO$_2$R' or —SO$_3$R' and Y' is —CN, —COOR', —COCH$_3$, —SO$_2$R' or —SO$_3$R', and R' is H or hydrocarbyl.

Preferred monomers of formula (I) for use in this invention are alpha-cyanoacrylates. These monomers are known in the art and have the formula

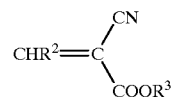

wherein R$^2$ is hydrogen or —CH=CH$_2$ and R$^3$ is a hydrocarbyl or substituted hydrocarbyl group; a group having the formula —R$^4$—O—R$^5$—O—R$^6$, wherein R$^4$ is a 1,2-alkylene group having 2–4 carbon atoms, R$^5$ is an alkylene group having 2—4 carbon atoms, and R$^6$ is an alkyl group having 1–6 carbon atoms; or a group having the formula

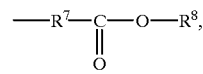

wherein R$^7$ is

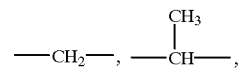

or —C(CH$_3$)$_2$— and R$^8$ is an organic radical.

Examples of suitable hydrocarbyl and substituted hydrocarbyl groups include straight chain or branched chain alkyl groups having 1–16 carbon atoms; straight chain or branched chain C$_1$–C$_{16}$ alkyl groups substituted with an acyloxy group, an alkoxy group, a halogen atom, a cyano group, a haloalkyl group or a haloaryl group; straight chain or branched chain alkenyl groups having 2 to 16 carbon atoms; straight chain or branched chain alkynyl groups having 2 to 12 carbon atoms; cycloalkyl groups; aralkyl groups; alkylaryl groups; and aryl groups.

The organic radical R$^8$ may be substituted or unsubstituted and may be straight chain, branched or cyclic, saturated, unsaturated or aromatic. Examples of such organic radicals include C$_1$–C$_8$ alkyl radicals, C$_2$–C$_8$ alkenyl radicals, C$_2$–C$_8$ alkynyl radicals, C$_3$–C$_{12}$ cycloaliphatic radicals, aryl radicals such as phenyl and substituted phenyl and aralkyl radicals such as benzyl, methylbenzyl and phenylethyl. Other organic radicals include substituted hydrocarbon radicals, such as halo- (e.g., chloro-, fluoro- and bromo-substituted hydrocarbons) and oxy- (e.g., alkoxy substituted hydrocarbons) substituted hydrocarbon radicals. Preferred organic radicals are alkyl, alkenyl and alkynyl radicals having from 1 to about 8 carbon atoms, and halo-substituted derivatives thereof. Particularly preferred are alkyl radicals of 4 to 6 carbon atoms.

In the cyanoacrylate monomer of formula (II), R$^3$ is preferably an alkyl group having 1–10 carbon atoms or a group having the formula —AOR$^9$, wherein A is a divalent straight or branched chain alkylene or oxyalkylene radical having 2–8 carbon atoms, and R$^9$ is a straight or branched alkyl radical having 1–8 carbon atoms. Examples of groups represented by the formula —AOR$^9$ include 1-methoxy-2-propyl, 2-butoxy ethyl, isopropoxy ethyl, 2-methoxy ethyl, and 2-ethoxy ethyl.

The preferred alpha-cyanoacrylate monomers used in this invention are 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, or 1-methoxy-2-propyl cyanoacrylate.

The alpha-cyanoacrylates of formula (II) can be prepared according to methods known in the art. Reference is made, for example, to U.S. Pat. Nos. 2,721,858 and 3,254,111, each of which is hereby incorporated by reference herein. For example, the alpha cyanoacrylates can be prepared by reacting an alkyl cyanoacetate with formaldehyde in a non-aqueous organic solvent and in the presence of a basic catalyst, followed by pyrolysis of the anhydrous intermediate polymer in the presence of a polymerization inhibitor. The alpha-cyanoacrylate monomers prepared with low moisture content and essentially free of impurities are preferred for biomedical use.

The alpha-cyanoacrylates of formula (II) wherein $R^3$ is a group having the formula $-R^4-O-R^5-O-R^6$ can be prepared according to the method disclosed in U.S. Pat. No. 4,364,876 to Kimura et al., which is hereby incorporated by reference herein. In the Kimura et al. method, the alpha-cyanoacrylates are prepared by producing a cyanoacetate by esterifying cyanoacetic acid with an alcohol or by transesterifying an alkyl cyanoacetate and an alcohol; condensing the cyanoacetate and formaldehyde or para-formaldehyde in the presence of a catalyst at a molar ratio of 0.5–1.5:1, preferably 0.8–1.2:1, to obtain a condensate; depolymerizing the condensation reaction mixture either directly or after removal of the condensation catalyst to yield crude cyanoacrylate; and distilling the crude cyanoacrylate to form a high purity cyanoacrylate.

The alpha-cyanoacrylates of formula (II) wherein $R^3$ is a group having the formula

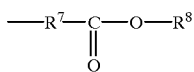

can be prepared according to the procedure described in U.S. Pat. No. 3,995,641 to Kronenthal et al., which is hereby incorporated by reference herein. In the Kronenthal et al. method, such alpha-cyanoacrylate monomers are prepared by reacting an alkyl ester of an alpha-cyanoacrylic acid with a cyclic 1,3-diene to form a Diels-Alder, adduct which is then subjected to alkaline hydrolysis followed by acidification to form the corresponding alpha-cyanoacrylic acid adduct. The alpha-cyanoacrylic acid adduct is preferably esterified by an alkyl bromoacetate to yield the corresponding carbalkoxymethyl alpha-cyanoacrylate adduct. Alternatively, the alpha-cyanoacrylic acid adduct may be converted to the alpha-cyanoacrylyl halide adduct by reaction with thionyl chloride. The alpha-cyanoacrylyl halide adduct is then reacted with an alkyl hydroxyacetate or a methyl substituted alkyl hydroxyacetate to yield the corresponding carbalkoxymethyl alpha-cyanoacrylate adduct or carbalkoxy alkyl alpha-cyanoacrylate adduct, respectively. The cyclic 1,3-diene blocking group is finally removed and the carbalkoxy methyl alpha-cyanoacry late adduct or the carbalkoxy alkyl alpha-cyanoacrylate adduct is converted into the corresponding carbalkoxy alkyl alpha-cyanoacrylate by heating the adduct in the presence of a slight deficit of maleic anhydride.

Examples of monomers of formula (II) include cyanopentadienoates and alpha-cyanoacrylates of the formula:

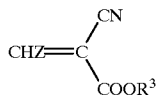

wherein Z is $-CH=CH_2$ and $R^3$ is as defined above. The monomers of formula (III) wherein $R^3$ is an alkyl group of 1–10 carbon atoms, i.e., the 2-cyanopenta-2,4-dienoic acid esters, can be prepared by reacting an appropriate 2-cyanoacetate with acrolein in the presence of a catalyst such as zinc chloride. This method of preparing 2-cyanopenta-2,4-dienoic acid esters is disclosed, for example, in U.S. Pat. No. 3,554,990, which is hereby incorporated by reference herein.

Preferred monomers are alkyl alpha-cyanoacrylates and more preferably octyl alpha-cyanoacrylates, especially 2-octyl alpha-cyanoacrylate. Monomers utilized in the present invention should be very pure and contain few impurities. That is, the monomers used in the present invention should preferably be of surgical grade.

The compositions of this invention may also include at least one plasticizing agent that imparts flexibility to the polymerized monomer formed on the wound or incision. The plasticizing agent preferably contains little or no moisture and should not significantly affect the polymerization of the monomer.

Examples of suitable plasticizers include, but are not limited to, acetyl tributyl citrate, dimethyl sebacate, triethyl phosphate, tri(2-ethylhexyl)phosphate, tri(p-cresyl) phosphate, glyceryl triacetate, glyceryl tributyrate, diethyl sebacate, dioctyl adipate, isopropyl myristate, butyl stearate, lauric acid, trioctyl trimellitate, dioctyl glutarate, mixtures thereof and the like. Preferred plasticizers are tributyl citrate and acetyl tributyl citrate.

The compositions of this invention may also include at least one acidic stabilizing agent that inhibits polymerization. Such stabilizing agents may also include mixtures of anionic stabilizing agents and free radical stabilizing agents.

Examples of suitable anionic stabilizing agents include, but are not limited to, sulfur dioxide, sulfonic acid, lactone, boron trifluoride, organic acids, alkyl sulfate, alkyl sulfite, 3-sulfolene, alkylsulfone, alkyl sulfoxide, mercaptan, alkyl sulfide, mixtures thereof and the like. Preferable anionic stabilizing agents are acidic stabilizing agents of organic acids such as acetic acid or phosphoric acid with acetic acid being a more preferable acidic stabilizing agent. The maximum amount of sulfur dioxide present in the adhesive composition should be less than 50 ppm.

Examples of suitable free radical stabilizing agents include, but are not limited to, hydroquinone, hydroquinone monomethyl ether, catechol, pyrogallol, benzoquinone, 2-hydroxybenzoquinone, p-methoxy phenol, t-butyl catechol, butylated hydroxy anisole, butylated hydroxy toluene, t-butyl hydroquinone, mixtures thereof and the like.

Suitable acidic stabilizing agents include those having $pK_a$ ionization constants ranging from about 0 to about 7, preferably from about 1 to about 6, and more preferably from about 2 to about 5.5. For example, suitable acidic stabilizing agents include, but are not limited to: hydrogen sulfide ($pK_a$ 7.0), carbonic acid ($pK_a$ 6.4), triacetylmethane ($pK_a$ 5.9), acetic acid ($pK_a$ 4.8), benzoic acid ($pK_a$ 4.2), 2,4-dinitrophenol ($pK_a$ 4.0), formic acid ($pK_a$ 3.7), nitrous acid ($pK_a$ 3.3), hydrofluoric acid ($pK_a$ 3.2), chloroacetic acid ($pK_a$ 2.9), phosphoric acid ($PK_a$ 2.2), dichloroacetic acid ($pK_a$ 1.3), trichloroacetic acid ($pK_a$ 0.7), 2,4,6-trinitrophenol (picric acid) ($pK_a$ 0.3), trifluoroacetic acid ($pK_a$ 0.2), mixtures thereof and the like.

When adding the above-mentioned weak acidic stabilizing agents to the adhesive composition, it has been discovered that the addition of plasticizing agents in amounts ranging from about 0.5 wt. % to about 16 wt. %, preferably from about 3 wt. % to about 9 wt. %, and more preferably from about 5 wt. % to about 7 wt. %, provides increased film strength (e.g., toughness) of the polymerized monomer over polymerized monomers having amounts of plasticizing agents and acidic stabilizing agents outside of the above ranges.

The concentration of the acidic stabilizing agents utilized may vary depending on the strength of the acid. For example, when using acetic acid, a concentration of 80–200 ppm (wt/wt), preferably 90–180 ppm (wt/wt), and more preferably 100–150 ppm (wt/wt) may be utilized. When using a stronger acid, such as phosphoric acid, a concentration range of 20–80 ppm (wt/wt), preferably, 30–70 ppm (wt/wt) and more preferably 40–60 ppm (wt/wt) may be utilized.

The compositions of this invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds useful in this invention include, but are not limited to, sulfites; bisulfites; mixtures of sulfites and bisulfites; ammonium sulfite salts; amines; amides; imides; nitriles; carbamates; alcohols; mercaptans; proteins; mixtures of amines, amides, and proteins; active methylene compounds such as cyclic ketones and compounds having a β-dicarbonyl group; heterocyclic ring compounds free of a carbonyl group and containing an NH group, with the ring made up of nitrogen or carbon atoms, the ring being unsaturated or, when fused to a phenyl group, being unsaturated or saturated, and the NH group being bonded to a carbon or a nitrogen atom, which atom is directly bonded by a double bond to another carbon or nitrogen atom; mixtures thereof and the like.

Bisulfites and sulfites useful as the formaldehyde scavenger compound in this invention include alkali metal salts such as lithium, sodium and potassium salts, and ammonium salts, for example, sodium bisulfite, potassium bisulfite, lithium bisulfite, ammonium bisulfite, sodium sulfite, potassium sulfite, lithium sulfite, ammonium sulfite, and the like.

Examples of amines useful in this invention include the aliphatic and aromatic amines such as, for example, aniline, benzidine, aminopyrimidine, toluene-diamine, triethylenediamine, diphenylamine, diaminodiphenylamine, hydrazines and hydrazide.

Suitable proteins include collagen, gelatin, casein, soybean protein, vegetable protein, keratin and glue. The preferred protein for use in this invention is casein.

Suitable amides for use in this invention include urea, cyanamide, acrylamide, benzamide, and acetamide. Urea is the preferred amide.

Suitable alcohols include phenols, 1,4-butanediol, d-sorbitol, and polyvinyl alcohol.

Examples of suitable compounds having a β-dicarbonyl group include malonic acid, acetylacetone, ethylacetone, acetate, malonamide, diethylmalonate or another malonic ester.

Preferred cyclic ketones for use in this invention include cyclohexanone or cyclopentanone.

Examples of suitable heterocyclic compounds for use as the formaldehyde scavenger in this invention are disclosed, for example, in U.S. Pat. No. 4,127,382 (Perry) which is hereby incorporated by reference herein. Such heterocyclic compounds include, for example, benzimidazole, 5-methyl benzimidazole, 2-methylbenzimidazole, indole, pyrrole, 1,2,4-triazole, indoline, benzotriazole, indoline, and the like.

A preferred formaldehyde scavenger for use in this invention is sodium bisulfite.

In practicing embodiments of this invention, the formaldehyde concentration reducing agent, e.g., formaldehyde scavenger compound, is added in an effective amount to the cyanoacrylate. The "effective amount" is that amount sufficient to reduce the amount of formaldehyde generated during subsequent in vivo biodegradation of the polymerized cyanoacrylate. This amount will depend on the type of active formaldehyde concentration reducing agent, and can be readily determined without undue experimentation by those skilled in the art.

The formaldehyde concentration reducing agent may be used in this invention in either free form, protected form (e.g., chemically protected), or in microencapsulated form.

When microencapsulated, the formaldehyde concentration reducing agent is released from the microcapsule continuously over a period of time during the in vivo biodegradation of the cyanoacrylate polymer.

For purposes of this invention, the microencapsulated form of the formaldehyde concentration reducing agent is preferred because this embodiment prevents or substantially reduces polymerization of the cyanoacrylate monomer by the formaldehyde concentration reducing agent, which increases shelf-life and facilitates handling of the adhesive composition during use.

Microencapsulation of the formaldehyde scavenger can be achieved by many known microencapsulation techniques. For example, microencapsulation can be carried out by dissolving a coating polymer in a volatile solvent, e.g., methylene chloride, to a polymer concentration of about 6% by weight; adding a formaldehyde scavenger compound in particulate form to the coating polymer/solvent solution under agitation to yield a scavenger concentration of about 18% by weight; slowly adding a surfactant-containing mineral oil solution to the polymer solution under rapid agitation; allowing the volatile solvent to evaporate under agitation; removing the agitator; separating the solids from the mineral oil; and washing and drying the microparticles. The size of the microparticles will range from about 0.001 to about 1000 microns.

The coating polymer for microencapsulating the formaldehyde concentration reducing agent should be polymers that undergo in vivo bioerosion, preferably at rates similar to or greater than the cyanoacrylate polymer formed by the monomer, and should have low inherent moisture content. Such "bioerosion" can occur as a result of the physical or chemical breakdown of the encapsulating material, for example, by the encapsulating material passing from solid to solute in the presence of body fluids, or by biodegradation of the encapsulating material by agents present in the body.

Examples of coating materials that can be used to microencapsulate the formaldehyde concentration reducing agent include, but are not limited to, polyesters, such as polyglycolic acid, polylactic acid, copolymers of polyglycolic acid and polylactic acid, polycaprolactone, poly-β-hydroxybutyrate, copolymers of epsilon-caprolactone and delta-valerolactone, copolymers of epsilon-caprolactone and DL-dilactide, and polyester hydrogels; polyvinylpyrrolidone; polyamides; gelatin; albumin; proteins; collagen; poly (orthoesters); poly(anhydrides); poly(alkyl-2-cyanoacrylates); poly(dihydropyrans); poly(acetals); poly (phosphazenes); poly(urethanes); poly(dioxinones); cellulose; starches; mixtures thereof and the like.

Examples of the surfactant that can be added to the mineral oil include those commercially available under the designations Triton x-100, Tween 20 and Tween 80.

The composition of this invention may further contain one or more adjuvant substances, such as thickening agents, medicaments, or the like, to improve the medical utility of the monomer for particular medical applications.

Suitable thickeners include, for example, polycyanoacrylates, polylactic acid, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylates and butadiene.

To improve the cohesive strength of adhesives formed from the compositions of this invention, difunctional monomeric cross-linking agents may be added to the adhesive compositions of this invention. Such crosslinking agents are known. Reference is made, for example, to U.S. Pat. No. 3,940,362 to Overhults, which is hereby incorporated by reference herein. Examples of suitable crosslinking agents include alkyl bis(2-cyanoacrylates), triallyl isocyanurates, alkylene diacrylates, alkylene dimethacrylates, trimethylol propane triacrylate, and alkyl bis(2-cyanoacrylates). A catalytic amount of an amine activated free radical initiator may be added to initiate polymerization of the monomer/crosslinking agent blend.

The compositions of this invention may further contain fibrous reinforcement and colorants, i.e., dyes and pigments. Examples of suitable fibrous reinforcement include PGA microfibrils, collagen microfibrils, cellulosic microfibrils, and olefinic microfibrils. Examples of suitable colorants include 1-hydroxy-4-[4-methylphenyl-amino]-9,10 anthracenedione (D+C violet No. 2); disodium salt of 6-hydroxy-5-[(4-sulfophenyl)axo]-2-naphthalene-sulfonic acid (FD+C Yellow No. 6); 9-(o-carboxyphenyl)-6-hydroxy-2,4,5,7-tetraiodo-3H-xanthen-3-one, disodium salt, monohydrate (FD+C Red No. 3); 2-(1,3-dihydro-3-oxo-5-sulfo-2H-indol-2-ylidene)-2,3-dihydro-3-oxo-1H-indole-5-sulfonic acid disodium salt (FD+C Blue No. 2); and [phthalocyaninato (2-)] copper.

Compositions employed in the present invention are preferably sterilizable by conventional methods that include, but are not limited to, autoclave or aseptic filtration techniques.

The invention is further illustrated by the following non-limiting examples.

EXAMPLES I–X

The adhesive compositions according to the present invention are prepared utilizing conventional mixing equipment. For example, the process may be conducted as follows:

To a surgical grade cyanoacrylate in a round-bottom flask is added a heat dissipating agent, and other formulation components as described herein. The resulting mixture is mechanically stirred until it is homogeneous.

In the following examples, various heat dissipating agents are utilized in adhesive compositions of the present invention that illustrate the effects on the exothermic reaction temperature of the composition. The monomer used in all of the Examples is 2-octyl cyanoacrylate. The results are compared against a control sample that included no heat dissipating agent. The results are set forth in Table I.

TABLE I

| Sample | Heat Dissipating Agent | Concentration (Wt %) | Average Temp (° C.) | Temp Decrease (° C.) |
|---|---|---|---|---|
| Control | | | 94 | |
| Example I | Diethyl Ether | 10 | 37 | |
| Example II | Diethyl Ether | 20 | 32 | |
| Example III | Pentane | 10 | 55 | |
| Example IV | Pentane | 20 | 46 | |
| Example V | BME* | 10 | 49 | |
| Example VI | BME* | 20 | 34 | |
| Example VII | TBME** | 10 | 38 | |
| Example VIII | TBME** | 20 | 35 | |
| Example IX | Acetone | 13 | 34 | |
| Example X | Acetone | 20 | 35 | |

*BME = Butyl methyl ether
**TBME = Tert-Butyl methyl ether

EXAMPLE XI

The process as conducted above was utilized with a 2-octyl cyanoacrylate with a solid heat dissipting agent, namely 2,2,6,6-tetramethyl-4-hepten-3-one. A control comprising 2-octyl cyanoacrylate with 6% by weight of acetyl tributyl citrate was used. The results are set forth in Table II.

TABLE II

| Sample | Heat Dissipating Agent | Concentration (Wt %) | Average Temp (° C.) | Temp Decrease (° C.) |
|---|---|---|---|---|
| Control | | | 85 | |
| Example II | TMH* | 13 | 74 | |

*TMH = 2,2,6,6-tetramethyl-4-hepten-3-one

What is claimed is:

1. A biocompatible monomer composition having a shelf life, comprising:
    A) at least one monomer, which forms a medically acceptable polymer; and
    B) an effective amount of at least about 1% by weight of at least one heat dissipating agent sufficient to reduce exothermic polymerization temperature increase of the composition.

2. A biocompatible composition according to claim 1, wherein the amount of heat dissipating agent added to the composition is sufficient to prevent necrosis of living tissue.

3. A biocompatible composition according to claim 1, wherein the heat dissipating agent is present in the composition in an amount of about 0.1 to about 70% by weight.

4. A biocompatible composition according to claim 1, wherein said reduction in temperature increase is about 1 to about 100° C.

5. A biocompatible composition according to claim 1, wherein the heat dissipating agent is in a solid or a liquid form.

6. A biocompatible composition according to claim 1, wherein the heat dissipating agent is at least one component selected from the group consisting of a volatile liquid, a solid having a melting point of from about 20° C. to about 150° C. and a solid having a sublimation point of from about 20° C. to about 150° C.

7. A biocompatible composition according to claim 1, wherein the heat dissipating agent is selected from the group consisting of potassium nitrate, sodium acetate trihydrate, sodium sulfate decahydrate, barium hydroxide octahydrate, calcium oxalate dihydrate, magnesium oxalate dihydrate, aluminum hydroxide, zinc sulfate, aluminum oxide, barium oxide, titanium oxide, manganese oxide, and calcium oxide; copper, lead, nickel, aluminum and zinc; carbon black and carbides; urea, paraffin wax and polyvinyl fluoride; 2-hydroxy-2-trimethylsilanyl-propionitrile, 1-fluoropentacyclo[6.3.0.02,6.03,10.05,9]undecane, 6,7-diazabicyclo[3.2.1]oct-6-ene, 5,5,6,6-tetramethylbicyclo[2.2.1]heptan-2-ol, complex of dimethyl magnesium and trimethylaluminum, N-benzyl-2,2,3,3,4,4,4-heptafluoro-butyramide, 3-isopropyl-5,8a-dimethyl-decahydronaphthalen-2-ol, 2-hydroxymethyl-1,7,7-trimethyl-bicyclo[2.2.1]heptan-2-ol, 3,5-dichloro-3-methyl-cyclopentane-1,2-dione, (5-methyl-2-oxo-bicyclo[3.3.1.]non-3-en-1-yl)-acetic acid, 4b,6a,11,12-tetrahydro-indeno[2,1-a]fluorene-5,5,6,6-tetracarbonitrile, tetracosafluoro-tetradecahydro-anthracene, 4,5-dichlorobenzene-1,2-dicarbaldehyde, bicyclo[4,3.1]dec-3-en-8-one, 3-tert-butyl-1,2-bis-(3,5-dimethylphenyl)-3-hydroxyguanidine, 1-[2,6-dihydroxy-4-methoxy-3-methylphenyl]butan-1-one, 2,3,6,7-tetrachloronaphthalene, 2,3,6-trimethylnaphthalene, dodecafluoro-cyclohexane, 2,2,6,6-tetramethyl-4-hepten-3-one, 1,1,1-trichloro-2,2,2-trifluoro-ethane, [5-(9H-beta-carbolin-1-yl)-furan-2-yl]methanol, 5-nitro-benzo[1,2,3]thiadiazole, 4,5-dichloro-thiophene-2-carboxylic acid, 2,6-dimethyl-isonicotinonitrile, nonafluoro-2,6-bis-trifluoromethyl-piperidine, (dimethylamino)difluoroborane, dinitrogen pentoxide, chromyl fluoride, and chromium hexacarbonyl; 1-methylcyclohexanol, phenyl ether, nonadecane, 1-tetradecanol, 4-ethylphenol, benzophenone, maleic anhydride, octacosane, dimethyl isophthalate, butylated hydroxytoluene, glycolic acid, vanillin, magnesium nitrate hexahydrate, cyclohexanone oxime, glutaric acid, D-sorbitol, phenanthrene, methacrylamide, fluorene, 4-hydroxybenzaldehyde, trans-stilbene, neopentyl glycol, pyrogallol, and diglycolic acid; and combinations thereof.

8. A biocompatible composition according to claim 1, wherein the composition is absorbable by living tissue.

9. A biocompatible composition according to claim 1, wherein the monomer is 1,1-disubstituted ethylene.

10. A method of applying to living tissue a biocompatible monomer composition, comprising:

A) applying to living tissue a biocompatible adhesive composition having a shelf life and comprising at least one monomer, which forms a medically acceptable polymer, and an effective amount of at least about 1% by weight of a heat dissipating agent to reduce exothermic polymerization temperature increase; and B) polymerizing the adhesive composition to form the medically acceptable polymer.

11. A method of applying to living tissue a biocompatible monomer composition, comprising:

A) applying to living tissue a biocompatible adhesive composition comprising at least one monomer, which forms a medically acceptable polymer, and an effective amount of a heat dissipating agent to reduce exothermic polymerization temperature increase; and B) polymerizing the adhesive composition to form the medically acceptable polymer, wherein said heat dissipating agent is at least one component selected from the group consisting of (i) a solid (ii) and a liquid selected from the group consisting of ethers, esters, ketones, chlorofluorocarbons, alkanes, alkenes and mixtures thereof.

12. A method according to claim 11, wherein the heat dissipating agent is premixed with the at least one monomer or is mixed with the at least one monomer immediately prior to application to the living tissue.

13. A method according to claim 10, wherein the composition contains said heat dissipating agent in an amount sufficient to prevent necrosis of living tissue.

14. A method according to claim 10, wherein the heat dissipating agent is present in the composition in an amount of about 0.1 to about 70% by weight.

15. A method according to claim 10, wherein said reduction in temperature increase is about 1 to about 100° C.

16. A method according to claim 10, wherein the heat dissipating agent is in a solid or a liquid form.

17. A method according to claim 10, wherein the heat dissipating agent is a volatile liquid.

18. A method according to claim 10, wherein the heat dissipating agent is selected from the group consisting of potassium nitrate, sodium acetate trihydrate, sodium sulfate decahydrate, barium hydroxide octahydrate, calcium oxalate dihydrate, magnesium oxalate dihydrate, aluminum hydroxide, zinc sulfate, aluminum oxide, barium oxide, titanium oxide, manganese oxide, and calcium oxide; copper, lead, nickel, aluminum and zinc; carbon black and carbides; urea, paraffin wax and polyvinyl fluoride; 2-hydroxy-2-trimethylsilanyl-propionitrile, 1-fluoropentacyclo[6.3.0.02,6.03,10.05,9]undecane, 6,7-diazabicyclo[3.2.1]oct-6-ene, 5,5,6,6-tetramethylbicyclo[2.2.1]heptan-2-ol, complex of dimethyl magnesium and trimethylaluminum, N-benzyl-2,2,3,3,4,4,4-heptafluoro-butyramide, 3-isopropyl-5,8a-dimethyl-decahydronaphthalen-2-ol, 2-hydroxymethyl-1,7,7-trimethyl-bicyclo [2.2.1]heptan-2-ol, 3,5-dichloro-3-methyl-cyclopentane-1,2-dione, (5-methyl-2-oxo-bicyclo[3.3.1.]non-3-en-1-yl)-acetic acid, 4b,6a,11,12-tetrahydro-indeno [2,1-a]fluorene-5,5,6,6-tetracarbonitrile, tetracosafluoro-tetradecahydro-anthracene, 4,5-dichlorobenzene-1,2-dicarbaldehyde, bicyclo[4,3.1] dec-3-en-8-one, 3-tert-butyl-1,2-bis-(3,5-dimethylphenyl)-3-hydroxyguanidine, 1-[2,6-dihydroxy-4-methoxy-3-methylphenyl]butan-1-one, 2,3,6,7-tetrachloronaphthalene, 2,3,6-trimethylnaphthalene, dodecafluoro-cyclohexane, 2,2,6,6-tetramethyl-4-hepten-3-one, 1,1,1-trichloro-2,2,2-trifluoro-ethane, [5-(9H-beta-carbolin-1-yl)-furan-2-yl]methanol, 5-nitro-benzo[1,2,3]thiadiazole, 4,5-dichloro-thiophene-2-carboxylic acid, 2,6-dimethyl-isonicotinonitrile, nonafluoro-2,6-bis-trifluoromethyl-piperidine, (dimethylamino)difluoroborane, dinitrogen pentoxide, chromyl fluoride, and chromium hexacarbonyl; 1-methylcyclohexanol, phenyl ether, nonadecane, 1-tetradecanol, 4-ethylphenol, benzophenone, maleic anhydride, octacosane, dimethyl isophthalate, butylated hydroxytoluene, glycolic acid, vanillin, magnesium nitrate hexahydrate, cyclohexanone oxime, glutaric acid, D-sorbitol, phenanthrene, methacrylamide, fluorene, 4-hydroxybenzaldehyde, trans-stilbene, neopentyl glycol, pyrogallol, and diglycolic acid; and combinations thereof.

19. A method according to claim 10, wherein the composition is absorbable by living tissue.

20. A method according to claim 10, wherein the monomer is 1,1-disubstituted ethylene.

21. A method according to claim 11, wherein the monomer and the heat dissipating agent are stored separately and are mixed during said applying step.

22. A biocompatible composition according to claim 1, wherein said heat dissipating agent is a volatile liquid.

23. A biocompatible composition according to claim 1, further comprising a component selected from the group consisting of an initiator, a thickener, a plasticizer, a colorant, a formaldehyde scavenger and combinations thereof.

24. A biocompatible composition according to claim 1, wherein the heat dissipating agent is an alkaline metal oxide selected from the group consisting of aluminum oxide, barium oxide, titanium oxide, manganese oxide, and calcium oxide.

25. A biocompatible composition according to claim 1, wherein the heat dissipating agent is a metal selected from the group consisting of copper, lead, nickel, aluminum and zinc.

26. A biocompatible composition according to claim 1, wherein the heat dissipating agent is carbon black or a carbide.

27. A biocompatible composition according to claim 1, wherein the heat dissipating agent is an organic compound selected from the group consisting of urea, paraffin wax and polyvinyl fluoride.

28. A biocompatible monomer composition, comprising:
   A) at least one monomer, which forms a medically acceptable polymer; and
   B) an effective amount of at least about 1% by weight of at least one heat dissipating agent sufficient to reduce exothermic polymerization temperature increase of the composition;
   wherein said heat dissipating agent does not increase the polymerization rate of the monomer in the composition.

29. A biocompatible monomer composition, comprising:
   A) at least one monomer, which forms a medically acceptable polymer; and
   B) an effective amount of at least one heat dissipating agent sufficient to reduce exothermic polymerization temperature increase of the composition,
   wherein said heat dissipating agent is at least one component selected from the group consisting of (a) a solid and (b) a liquid selected from the group consisting of ethers, esters, ketones, chlorofluorocarbons, alkanes, alkenes and mixtures thereof.

30. A method of applying to living tissue a biocompatible monomer composition comprising:
   A) applying to living tissue a biocompatible adhesive composition comprising at least one monomer, which forms a medically acceptable polymer, and an effective amount of at least about 1% by weight of a heat dissipating agent to reduce exothermic polymerization temperature increase, wherein said heat dissipating agent does not increase the polymerization rate of the monomer in the composition; and
   B) polymerizing the adhesive composition to form the medically acceptable polymer.

31. A biocompatible composition according to claim 29, wherein the heat dissipating agent is a solid having a sublimation point from about 20° C. to about 160° C.

32. A biocompatible composition according to claim 29, wherein the heat dissipating agent is a solid having a melting point of from about 20° C. to about 160° C.

* * * * *